United States Patent [19]
Thomson

[11] Patent Number: 5,444,254
[45] Date of Patent: Aug. 22, 1995

[54] FLEXIBLE RADIATION PROBE

[75] Inventor: Ian Thomson, Ottawa, Canada

[73] Assignee: Thomson and Nielsen Electronics Ltd., Canada

[21] Appl. No.: 72,710

[22] Filed: Jun. 7, 1993

Related U.S. Application Data

[63] Continuation-in-part of Ser. No. 898,074, Jun. 12, 1992, abandoned.

[51] Int. Cl.⁶ .................................................. G01T 1/24
[52] U.S. Cl. ........................ 250/370.07; 250/370.14
[58] Field of Search ............... 250/370.07, 370.14, 250/370.01, 371; 128/659

[56] References Cited

U.S. PATENT DOCUMENTS

| | | | |
|---|---|---|---|
| 4,678,916 | 7/1987 | Thomson | 250/370.07 |
| 4,976,266 | 12/1990 | Huffman et al. | 250/370.07 |
| 5,006,714 | 4/1991 | Attix | 250/368 |

Primary Examiner—Paul M. Dzierzynski
Assistant Examiner—Richard Hanig
Attorney, Agent, or Firm—Hayes Soloway Hennessey Grossman & Hage

[57] ABSTRACT

This invention describes a flexible radiation probe which has a pair of insulated gate field effect transistors integrated into the same substrate each having a gate, source and drain. The transistors are mounted at the end of a flexible circuit board. The flexible circuit board has conductive tracks which connect the gate, source and drains of each of the transistors to a connection at an opposite end of the flexible circuit board. This connection end may then be connected to a suitable differential biasing circuit for biasing the transistors, and a circuit for reading the differential threshold voltages of the transistors. This differential threshold voltage being indicative of radiation received by the transistors when exposed in the bias mode. The flexible circuit allows the probe to be used in catheters or similar medical equipment.

37 Claims, 4 Drawing Sheets

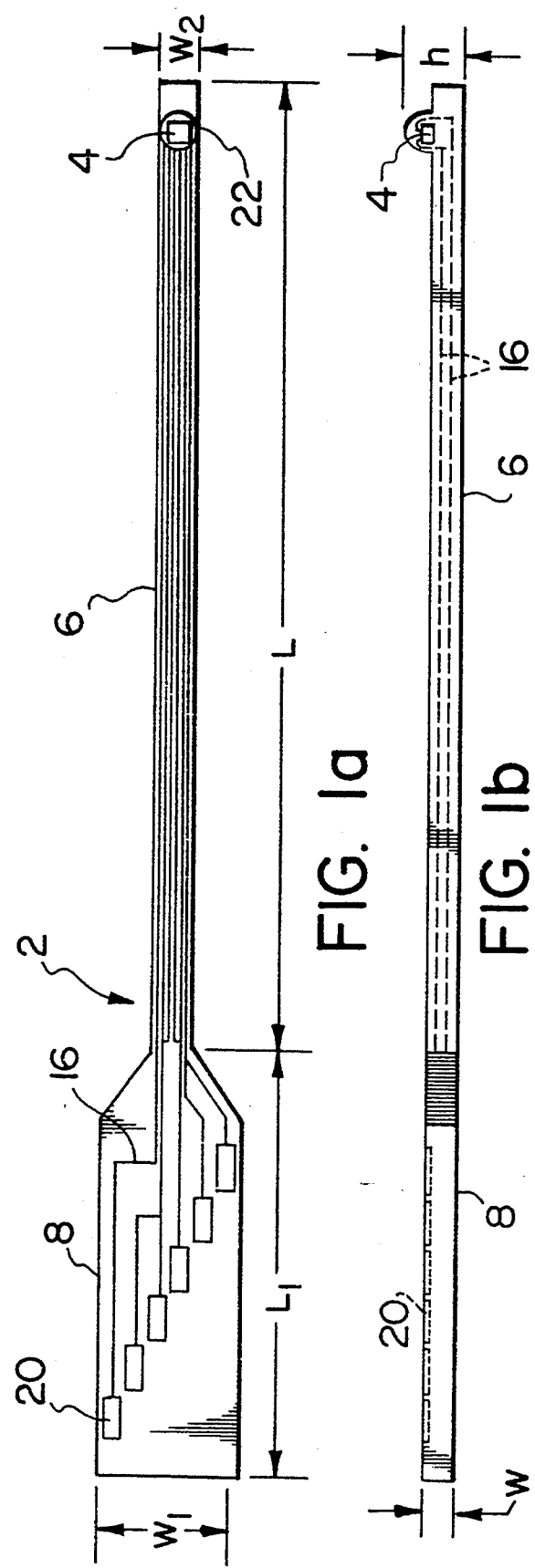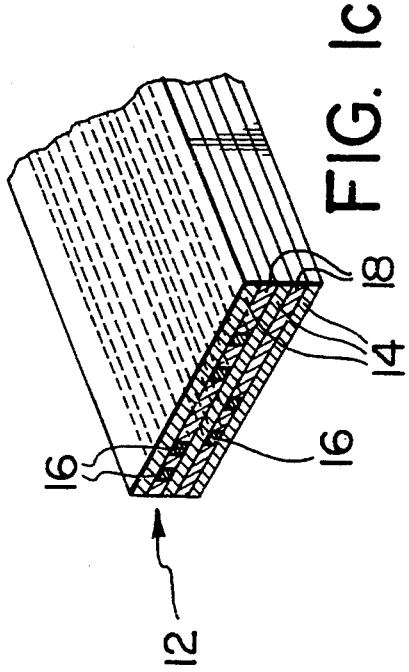

FLEXIBLE RADIATION PROBE

This is a continuation-in-part of U.S. application Ser. No. 898,074, filed Jun. 12, 1992, now abandoned.

FIELD OF THE INVENTION

This invention relates to flexible packaging for miniature metal oxide semiconductor field effect transistor (MOSFET) and more particularly to packaging for a MOSFET sensor probe used as a radiation dosimeter.

BACKGROUND OF THE INVENTION

The use of MOSFETs for detecting radiation is well known. It is understood that the threshold voltage of a MOSFET, or as it is sometimes called an insulated gate field effect transistor (IGFET) varies with exposure to radiation and therefore provides a useful building block in the design of dosimeters. The theory behind the use of these MOSFET dosimeters has been described in a number of papers some of which have been authored by the inventor. A paper entitled "Radiation Dosimetry with MOS.Sensors" by Ian Thomson, R. E. Thomas and L. Berndt, published in "Radiation Protection Dosimetry", Vol. 6, No. 1, pp. 121–124, December, 1983, and a paper entitled "Semiconductor MOSFET Dosimetry", published in the proceedings of the Health Physics Society 1988 Annual Meeting presents the theory behind MOSFET dosimeters, as well as experimental results with response to radiation of different kinds. These papers provide useful information on the background of this application.

Various configurations of MOSFETs have been implemented in the prior art in order to measure the amount of radiation dose received, while at the same time overcoming the numerous problems which limit the accuracy and stability of these devices. A recent implementation of a direct reading dosimeter using IGFETs is described in the inventor's U.S. Pat. No. 5,117,113 dated May 26, 1992. This patent discloses a radiation dosimeter having a pair of IGFETs integrated into the same silicon substrate, in which each of the transistors are operable in a bias mode and a test mode. A circuit element is provided for determining, during the test mode, the difference in the threshold voltages of the transistors, whereby the difference voltage is indicative of the radiation dose, and a circuit element is provided for continuously switching the transistors between the bias mode and the test mode, whereby the period of operation of the transistors in the test mode time period is small in comparison to the period of operation of the transistors in the bias mode.

There are a number of applications that require the use of a dosimeter to measure radiation. The sensitivity of a MOSFET to radiation is dependent upon the thickness of the gate oxide and the gate bias. By placing a small voltage, example 3 to 10 volts, on the gate of a MOSFET the sensitivity of the sensor can be enhanced.

MOSFETs of the type disclosed in the U.S. Pat. No. 5,117,113 would have to be mounted on a suitable package or substrate. Generally this takes the form of a standard IC package such as an 8 pin dual in line package (DIP). This type of packaging is adequate for the applications such as portable dosimeters or even badge type dosimeters.

A standard 8 pin DIP packaging is too bulky in uses such as in vivo radiation measurement. It is generally desirable for the dosimeter to be attached to a patient or inserted into a patient. In the latter case, this may require the use of a catheter where sterile conditions apply. U.S. Pat. No. 4,976,266 to Huffman et al. discloses a method and apparatus for in vivo radiation measurements which uses a MOSFET dosimeter. A disadvantage of the Huffman device is that it requires the separation of the MOSFETs by having a single MOSFET in a probe and another matched MOSFET outside the probe in order to provide temperature compensation. A compensation circuit is connected with this matched unirradiated MOSFET to operate at a current designed to eliminate temperature dependence of the device. However the human body has a much higher temperature than ambient temperature and it is likely that Huffman does not achieve the temperature compensation which is required of this type of application since any flexing of the catheter, particularly near the MOSFET, is likely to break the lead wire to the MOSFET. A further disadvantage with the Huffman device is the mounting of the MOSFET within the catheter with an epoxy which itself is limited in application. Further, the MOSFET is rigidly mounted which further limits the possible uses of the dosimeter. Since the threshold voltage of the MOSFET increases with cumulative dose and cannot be re-set to its original value, the dosimeter is generally discarded after a number of exposures. In the case of current MOSFET dosimetry systems when a saturation level of 20,000 cGy is reached the dosimeter is discarded. This means that for radiotherapy exposures of 200 cGy, the dosimeter may be used up to 100 times before it is discarded. In the case of higher dose exposures, such as in bracytherapy, the dosimeter may be used only 20 times or less.

A major disadvantage of Huffman and current devices is that they are not intended for large scale manufacture and thus the cost of these dosimeters does not justify use on a routine basis.

Furthermore there is a requirement for radiation workers to wear dosimeters at their extremities where these extremities are likely to receive higher doses than their whole body badges. Examples include technicians who work in the manufacture of radioisotopes, and technicians in nuclear medicine departments of hospitals who administer radioisotopes, physicians and nurses who work in the X-ray beam with fluoroscopy procedures and nuclear plant workers.

The annual dose allowed to extremities is 50 rems, as opposed to 2 rems for whole body since the extremities are less susceptible to negative effects of radiation than the organs in the body. The current requirements for lowest detectable levels for extremity dosimeters is 250 mrem (0.25 rem,) and the maximum is 10 rem as determined by the "U.S. Department of Energy-Standard for the Performance Testing of Extremity Dosimetry" draft May 4, 1991 (Rev 4). (Radiotherapy dose units used earlier were in cGy and we assume for simplicity that 1 rem=1 cGy.)

The most commonly used extremity dosimeter is a TLD, which is fixed to the wrist or fingers of the worker with adhesive tape or special finger ring type holders. Some disadvantages of this approach are:

(i) TLD extremity dosimeters suffer from the same drawbacks as other TLD dosimeters in that they can only be read with a special laboratory instrument. The crystals must be removed from their holders and manually handled. This is a relatively expensive slow process and, once read, the dose information is erased. In addition, identification can be lost once the crystal is removed from its holder which may contain an identification tag. In some applications, daily dose readings are carried out, thus requiring the facility to have twice as many dosimeters as workers since reading is carried out in a laboratory.

(ii) Extremity TLD dosimeters are generally too large to wear at the fingertips, which is the area of highest dose in most handling operations. A finger ring or wrist type is most commonly used in this application.

(iii) One of the main types of radiation of interest for extremity dosimetry is beta particles. These particles travel a short distance in material. Placement on the wrist or on a finger ring will not give an accurate measure of the dose to finger tips or thumbs. The dose at the wrist, for example, may be orders of magnitude different from that at the thumb.

(iv) Normal TLD crystals are too thick to adequately measure all energies of beta particles. The performance of TLD dosimeters is, therefore, not uniform with different types of radiation such as beta particles and X-rays. There also exists the need for a dosimeter which can be attached to a person's extremities (e.g. fingers, hands, head,) to measure personal radiation dose.

There therefore still exists a need for a miniature dosimeter that is capable of being used, for example, in vivo radiation measurement or which can be bent into any configuration to conform the sensor to its measuring environment. The sensor must also be capable of compensating for a wide variation in temperature and must also be sufficiently cost effective to justify its large scale use.

There are also times when it may be inconvenient to have many wires leading from the flexible circuit to direct reading circuitry. For instance, in radiotherapy, it is desirable to keep material on the patient to a minimum. At present thermoluminescence TLDs are used to measure the dose received by a patient. However, they often take hours to read and consequently pose further discomfort to an already uncomfortable situation.

There also exists a need in, for example, radiosurgery for a dosimeter which has high spatial resolution.

SUMMARY OF THE INVENTION

This invention seeks to provide packaging for a MOSFET, which is relatively easy to manufacture and which also exhibits a high degree of spatial resolution, while at the same time being extremely flexible.

In accordance with this invention there is provided a flexible radiation probe comprising:

a pair of insulated gate field effect transistors integrated into the same semiconductor substrate each having a gate, source and drain; and an elongate flexible member for supporting the transistors at a first end thereof, and for electrically connecting the gate, source and drains of each of the transistors to a second end remote to the first end, the second end being adapted for connection to external circuitry.

A further embodiment provides for a radiation dosimeter comprising:

flexible member having a plurality of electrical connection tracks extending between first and second ends thereof;

a semiconductor radiation sensor supported on the first end of the flexible member, the sensor having a pair of insulated gate field effect transistors integrated into the same substrate each having a gate, source and drain, and the electrical connection tracks for connecting to a respective one of the source, drain and gate; and means connectable to the second end of the flexible member for differentially biasing the transistors so that one of the transistors is more sensitive to ionising radiation than the other of the transistors during exposure of the transistors to radiation.

A further feature provides for a method for monitoring of radiation applied to a body comprising the steps of:

(i) inserting into the body a flexible radiation probe having a flexible member including a plurality of electrical connection tracks extending between first and second ends thereof and a radiation sensor supported at a first end of the flexible member, the sensor having a pair of insulated gate field effect transistors integrated into the same substrate each having a gate, source and drain, the electrical connection tracks connecting the source, drain and gate to the second end;

(ii) periodically biasing the transistors differentially and reading out the differential threshold voltage between the transistor through the flexible member.

BRIEF DESCRIPTION OF THE DRAWINGS

These and other features of the invention will become apparent, by way of example, from the following description in which reference is made to the appended drawings wherein:

FIGS. 1(a) and (b) show a top and side view, respectively, of a flexible sensor according to the present invention;

FIG. 1(c) shows a magnified view of part of the flexible sensor as shown in FIGS. 1(a) and (b);

DESCRIPTION OF A PREFERRED EMBODIMENT

Figure 2:
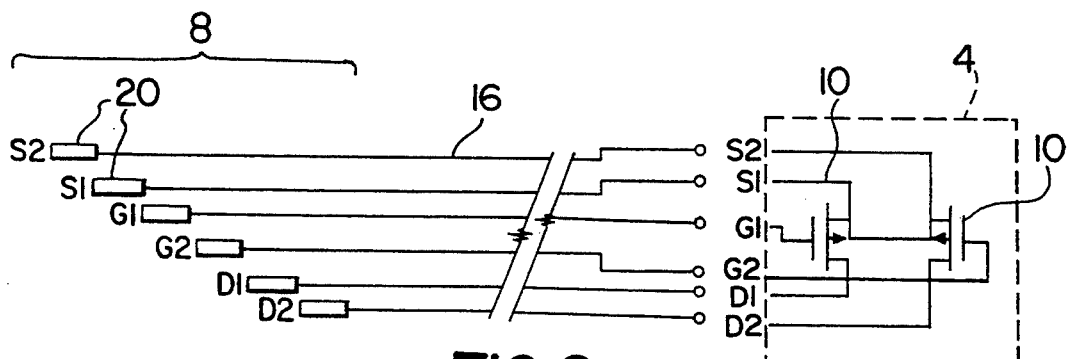
FIG. 2 is an electrical schematic diagram showing electrical connections for a pair of IGFETs according to the present invention.

Referring to FIGS. 1(a) and (b) a flexible radiation probe is shown generally by numeral 2. The probe has a radiation sensor 4, which is supported on a first end of an elongated flexible member or circuit board 6. The radiation sensor 4 is comprised of a pair of IGFET 10 transistors shown schematically in FIG. 2. These transistors are preferably of the same type and are fabricated in the same semiconductor die in order that they may have the same temperature variation characteristics, the same substrate resistivity and the same slow surface states prior to radiation. Each of the IGFETs 10 have a gate, source and drain terminals and are labelled G1, S1, D1 and G2, S2, and D2, respectively. The common substrate is connected internally in the IGFETs to their sources S1 and S2.

Figure 3B:
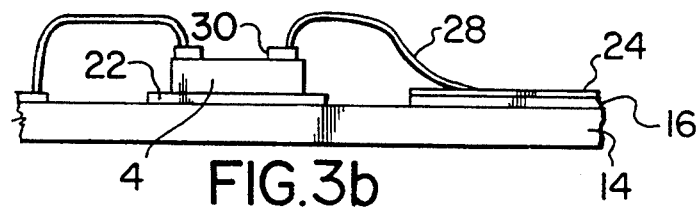
FIG. 3(b) is a schematic drawing showing bonding of leads to an IGFET, according to the present invention.

Referring back to FIGS. 1(a), (b) and more particularly FIG. 1(c), the flexible circuit board 6 is composed of a multilayer sandwich structure of alternately superposed polyimide film 14 and layers of copper connection tracks 16. Each layer of the sandwich structure is held together by epoxy 18. Polyimide film is used in the preferred embodiment, however any other suitable material which may be bent a number of times without damage may be used. A suitable polyimide film is kapton TM. Each of the conductive copper tracks 16 are each bonded to a respective one of the IGFET terminals as shown in FIG. 3(b). The conductive copper tracks 16 are gold plated at least on an upper surface in the vicinity of the first end to form bonding pads 24 so that wires 28 may be bonded from these tracks 16 to aluminum metallization pads 30 on the top surface of the IGFET die. The bonding wire 28 is generally 25 $\mu$m diameter, gold or aluminum. The flexible circuit 6 is enlarged at a second end 8 remote to the first end. In order that the probe may be connected to suitable external circuitry, a plurality of connector pads 20 are provided thereat. Each pad is 5 mm long by 1 mm wide and connects to a respective one of the copper tracks. The above described arrangement is also shown schematically in FIG. 2.

For the probe to be used in catheters or the like the flexible circuit must be made as small as possible. Thus the width $w_2$ of flexible circuit board 6 is preferably not much larger than the width of the radiation sensor 4 which itself is less than 2.2 mm on edge. A preferred length L of the flexible circuit 6 may be varied depending on where it is to be placed and how the radiation probe 2 is to be used. If, for example, the flexible circuit 6 is to be placed in the catheter (not shown) for use in brachytherapy, the flexible circuit may be 10 to 15 cm in length. It is preferred that the thickness w of flexible circuit 6 be very small, and at least less than 0.3 mm.

Figure 3A:
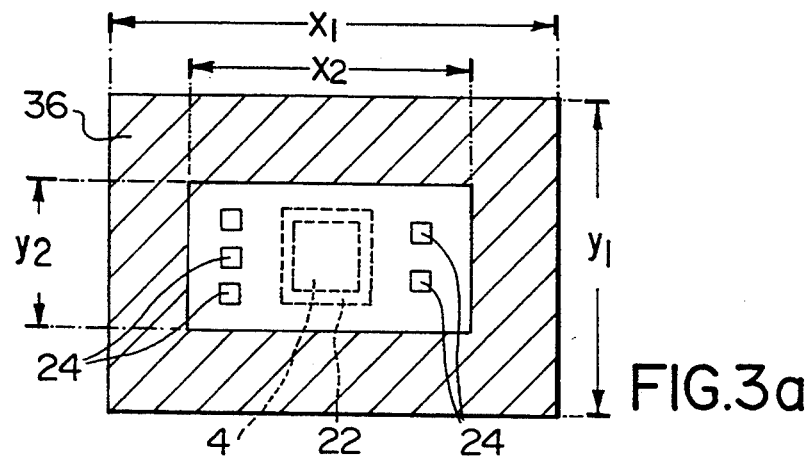
FIG. 3(a) is a top view of a semiconductor die which is mounted according to the present invention.

In the embodiment shown in FIGS. 1(a), (b) and (c) the dimensions for the flexible radiation probe 2 are:
L=24.4 cm
w=0.03 cm
h=0.1 cm
$L_1$=4.4 cm
$w_1$=0.69 cm
$w_2$=0.22 cm The sensor 4 is generally covered with epoxy, which increases the height h of the sensor 4 to approximately 0.1 cm. In the preferred embodiment the copper conducting tracks 16 are composed of 0.002–0.01 cm electrodeposited or rolled/annealed copper. The IGFET semiconductor chip die 4 is epoxied to a 0.025 $cm^2$ gold pad 22 which in turn is bonded to a rigid circuit board material. Five gold bonding pads 24, each 0.003 $cm^2$ in area, 1 $\mu$m in thickness, surround the IGFET as shown in FIG. 3(a). Once the semiconductor die 10 has been epoxied into place onto the gold pad 22, wire bond 28 connections are made from the semiconductor metallization pads 30 to the respective bonding pads 24 and the semiconductor is covered with an epoxy 32, such as hysol TM as shown cross-section in FIG. 4(a).

Figures 4A, 4B:
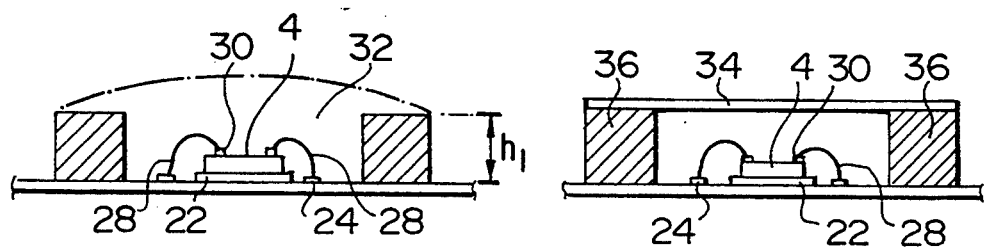
FIG. 4(a) is a cross-sectional view of a packaging for a semiconductor.
FIG. 4(b) is a further embodiment of a semiconductor packaging.

The epoxy covered sensor of FIG. 4(a) is adequate for receiving x-rays and gamma rays, however in some applications such as for example in measuring (beta particle) radiation to the skin of a human body this packaging is inadequate.

A suitable packaging for beta particle measurement is shown in FIG. 4(b). One key requirement for beta particle measurement is that the sensor must measure the dose behind a shield which has the equivalent thickness of (70 $\mu$m of tissue) which is equivilant to 7 mg/cm2. The average thickness of the epidermis (outer layer of human skin) is 70 $\mu$m.

This is generally achieved by placing the IGFETs 10 in a package having a foil lid 34. As described earlier, the semiconductor die is bonded to the end of the flexible material and wire bond connections are made as before. In addition thereto an annular wall 36 is constructed around the semiconductor die to form a "well" by bonding insulating material such as printed circuit board to the flexible circuit as shown in FIG. 4(b) and FIG. 3(a). The foil lid 34 generally comprising aluminum or metallized Mylar TM of appropriate thickness is bonded to the top of the wall, in order to protect the chip and provide a means for beta particles to enter the package.

The IGFETs are known to respond to beta particles in the same way as other types of radiation and over a wide range of energies. This is because of the extremely thin active region of the device (the silicon dioxide is <1 $\mu$m thick) thus beta particles down to 20 keV can be detected with unshielded dosimeters. Thick dosimeters such as TLDs have poorer performance with low energy beta particles. The thinnest TLD crystals commercially available for extremity dosimetry are about 25 m thick.

The extremity dosimeter previously described can be used to monitor skin dose from X-rays and gamma rays, but can also be simplified for these applications. The packaging as shown in FIG. 4(a) is less expensive to make than using a 70 $\mu$m window of FIG. 4(b) and may be used in applications where it is known that only X-rays or gamma rays exist. In nuclear medicine, for example, over 90% of the radiation exposure is due to the use of Tc99m, which emits X-rays at 140 keV. A simple epoxy covered sensor with or without a "well" is perfectly adequate for this single-use application.

The typical dimensions for a sensor as shown in FIG. 3(a) are:
$x_1$=0.274"
$x_2$=0.174"
$y_1$=0.185"
$y_2$=0.085"
$h_1$=0.05"

Figure 7:
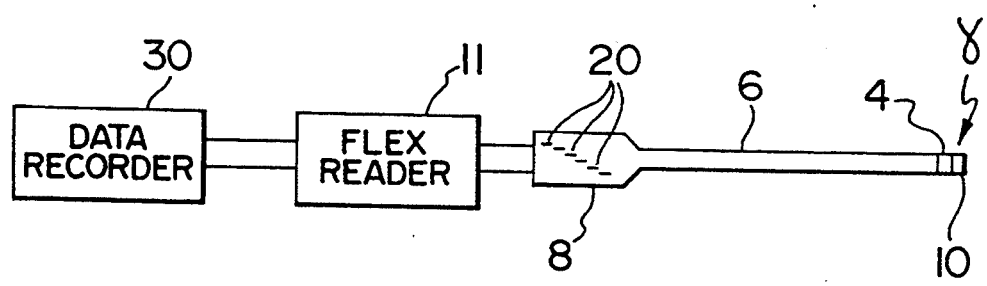
FIG. 7 is a schematic drawing of a direct reading dosimeter according to an embodiment of the present invention.

In use, the IGFETs are exposed to radiation while one transistor is biased relative to the other transistor and it has been found that more charge will accumulate upon radiation under the gate of the biased transistor compared to that of the unbiased transistor, thereby shifting its threshold voltage by a greater amount. By measuring the difference in threshold voltages it is possible to determine the radiation received by the IGFETs 10. In practice, an external circuit 11, as shown in FIG. 7, provides the bias for the IGFETs 10. This circuit 11 operates the IGFETs in a bias mode and a read mode. A circuit and method for performing the read and bias mode operations is described in the inventor's U.S. Pat. No. 5,117,113.

The IGFETs 10 are in bias mode 97% of the time, making the sensor sensitive to radiation. The other 3% of the time the sensor is placed into a read mode. In this manner, a direct reading can be taken and the radiation dose can be monitored in real time. This would be of particular interest when a radiotherapy machine is to be checked for beam flatness. The medical physicist often has to shape the beam using collimators. This is often time consuming using ionisation chambers or thermoluminescence devices (TLDs). It is envisioned that the flexible dosimeter connected to direct reading circuitry will replace these TLDs and increase the efficiency of the beam shaping process. An array of flexible probes 2 may be used to monitor the beam in real time and irradiation iterations could be performed without interruptions.

There are several advantages to using a direct reading circuit. The most apparent is decreased time spent reading absorbed dose either to patients or phantoms. Traditionally TLDs are used however they take several hours to be read. With the flexible dosimeter connected to direct reading circuitry more patients can be treated thus increasing the efficiency of the radiotherapy clinic. Another advantage is that the direct reading circuit could also be interfaced with a data recorder or a computer and absorbed dose could be monitored and recorded. This would be useful when a patient has been implanted with either radioactive beads or wires. Often the implant may last for a number of days with doses of several thousand of rads. Currently the inventor is not aware of any direct-reading method to measure absorbed dose for these patients. Post radiation stability may also be enhanced by using a test/bias circuit.

Figure 5A:
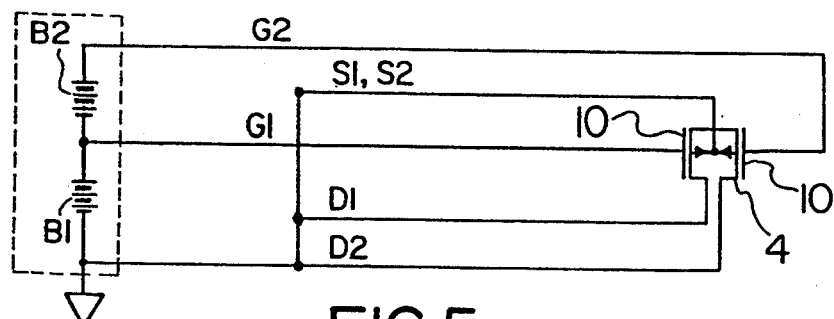
FIG. 5(a) is an electrical schematic drawing showing the connection of a pair of IGFETs for a passive dosimeter.
Figure 5B:
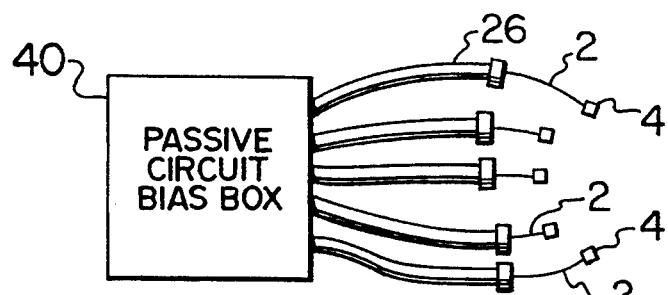
FIG. 5(b) is a schematic drawing of a passive dosimeter using a plurality of flexible sensors according to the invention.

The read/bias circuitry requires a large number of wires (six) leading from the flexible probe 2 to the read/bias circuitry. There are times however when it is more convenient to have few wires leading from the flexible radiation probe 2 to the read/bias circuitry. For instance, in radiotherapy, it is desirable to keep the material on the patient to a minimum. FIGS. 5(a) and (b) show a configuration for this application. The IGFETs 10 are placed in their most sensitive mode by placing a small bias voltage on the gate G1 and G2, respectively of each IGFET 10. A bias source such as a hearing aid battery B1 and B2 are connected in series with the positive terminal of a battery B2 connected to the gate G2 of a IGFET 10 and with the other terminal of the battery B1 connected to the gate G1 of the other IGFET 10. The sources S1 and S2 and drains D1 and D2 are connected together as shown schematically in FIG. 5(b). With the IGFETs 10 in their bias mode there is no current to the gate oxide thus the lifetime of the batteries B1 and B2 is essentially their shelf life. After irradiation, the flexible radiation probe 2 is disconnected from the bias batteries B1 and B2 and is connected to a readout circuit (not shown). The read out circuit may provide the user with the dose received by the IGFETs 10 and its past radiation history (example cumulative dose). In order to increase the sensitivity of the pair to measure lower doses, the differential bias is increased by means of more batteries from typically 6 V/3 V to 15 V/3 V. This increases the sensor differential sensitivity from 1 mV/rem to approximately 4 mV/rem thus increasing the signal to the reader.

There are applications which require multiple passive flexible radiation probes. In this instance as shown in FIG. 5(a) a passive circuit bias box 24 is used to provide the similar bias levels of the batteries B1 and B2 of FIG. 5(b). Each of the multiple flexible radiation probes 2 may be connected via a suitable cable 26 to the passive circuit bias box 24.

In the case of an extremity dosimeter for personal use, the bias box may also include a semiconductor memory device (not shown) such as an EEPROM. This device only requires power when it is being read from or written to. The memory may be used to permanently store data such as:

(i) Identification of the dosimeter and, if required, the user. Where dosimeters are not shared by different workers, the wearer's employee number or other unique identifier is written into this memory.
(ii) The dose history of the dosimeter, so that this information may be read by any other reader and is not reader specific.
(iii) Calibration information for the dosimeter, such as the exact calibration factor (mV/rem).
(iv) Other data which may be required to calculate dose or identify the wearer or location of the dosimeter. This configuration of the flexible radiation probe 2 is known as a passive flexible radiation probe.

Figure 6A:
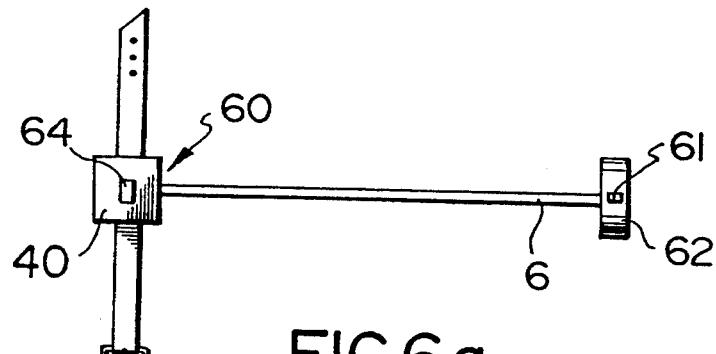
FIG. 6(a) is a schematic top view of an extremity dosimeter.
Figure 6B:
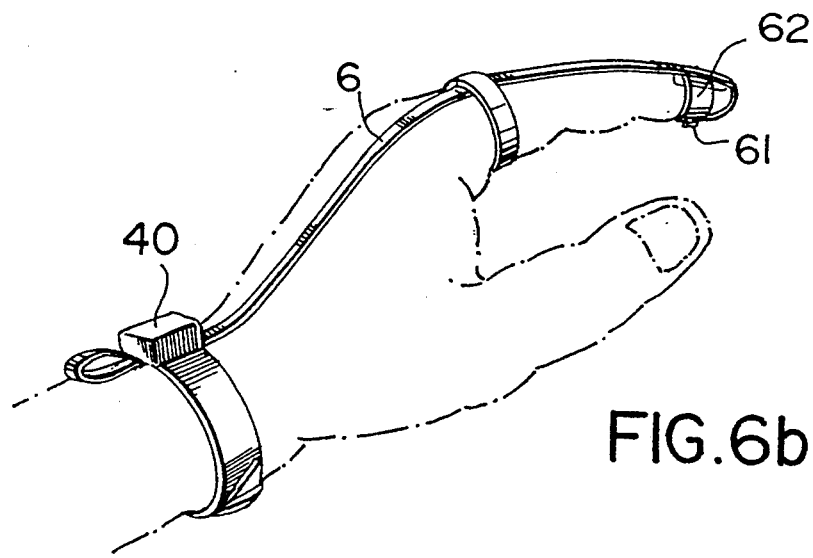
FIG. 6(b) is a schematic view showing a use of the dosimeter of FIG. 6(a)

In the case of an extremity dosimeter as shown in FIGS. 6(a) and 6(b), a relatively small passive bias box 28 is attached to the second end 60 of the flexible member 6. The bias box is typically attached to the wrist for hand extremities, but may also be attached to other parts of the body for other extremities (e.g. leg, head or feet). The sensor end 61 is positioned on the extremity using the tabs 62 to fasten around a finger as shown in FIG. 6(b). The position of the sensor at the end of the flexible member can be determined by the user e.g. finger tip, knuckle joint etc. In many cases, a protective glove (not shown) will also be worn on top of the dosimeter and this helps to keep the dosimeter in place.

In this configuration the dosimeter is used as follows. The dosimeter and its bias box 28 are electrically connected by a connector 64 on the bias box to the reader (not shown) which measures the differential threshold voltage of the MOSFET pair as described previously. The dosimeter is then worn for a period of time, typically a work period of one day, and the device is read again. The difference in the differential threshold voltages is proportional to the radiation dose received by the dosimeter. A dosimeter user can carry out a reading in less than 1 minute in the field, thus requiring only one dosimeter per worker.

The reader for this application is different from that for radiotherapy in that it must be able to read smaller differential MOSFET voltages than is required for radiotherapy since the doses in extremity dosimetry are much smaller than in therapy. This means that, with 4 mV/rem, we require to measure 0.8 mV (i.e. 800 uV) to correspond to 200 mrems. In practice, an electronic reading instrument of the type described for the radiotherapy system with increased voltage amplification can read to 5 uV, which is more than adequate as this corresponds to approximately 1 mrem.

The reader must also be capable of measuring the bias on the MOSFETs and indicating if the batteries require changing. It must read and write the information described above in the EEPROM memory device and print this out to give a hardcopy and/or transfer it electronically to another device such as a computer.

A simplified version of the reading circuitry (not shown) may also be included in the bias box 40 so that the wearer may get a direct reading of the radiation dose. This may have advantages in potentially dangerous radiation fields where an alarm may be required. This would mean that the reading circuitry would require only a differential threshold measurement and alarm function. The main reader would still be used for all other functions. This approach would not be used in all applications as the normal mode is to leave the dosimeter and glove on until the end of a work period.

Beam Quality Checks

Cobalt-60 and linear accelerators are often used in radiotherapy. Traditionally, ionization chambers, Thermoluminescence Dosimeters and/or films are most often used to measure the beam profile. Good spatial resolution of absorbed dose measurement is needed, and in the measurement of high absorbed dose gradients it is essential. It is in this area that the IGFET dosimeter has its greatest advantages over the above mentioned technologies. The IGFET sensor 4 area can be made less than 1 mm by 1 mm. It is envisioned that an array of flexible circuits can be positioned to measure the profile of a radiation beam in real time. This would greatly enhance the efficiency of the beam profiling process.

Phantom Dosimetry

In radiotherapy, the specification of the complete absorbed dose distribution within the radiation beam in a phantom is a prerequisite for calculating the prescribed absorbed dose to the target volume in the patient. It is envisioned that the direct reading flexible radiation probe 2 can be implanted at various locations in a phantom to measure absorbed dose. With this method the phantom does not have to be disassembled. The IGFETs can be read while still in the phantom and further beam modifications can take place.

In Vivo

In vivo measurements can be divided into five classes.

(i) Entrance absorbed dose.

These are mainly to check the machine output, the absorbed dose distribution across the patient and the positioning of shielding in relation to the position of the patient. The excellent spatial resolution of the flexible IGFET sensor may be exploited in this instance and greatly reduce set up time and enhance beam time efficiency.

(ii) Intra-cavity absorbed dose measurements

The absorbed dose within a body cavity (e.g. the mouth, nasopharynx, vagina, rectum, etc) can be measured using the flexible radiation probe 2. The flexible probe 2 may, if required for sterility reasons, first be placed within a catheter (not shown) and then placed within the body cavity (not shown). The flexible probes 2 are useful in that they are temperature independent, as described in U.S. Pat. No. 5,117,113. In this manner the flexible dosimeter can be read in real time or placed as a passive dosimeter and read periodically.

(iii) Individual spared organ absorbed dose measurements.

The absorbed dose to spared (shielded) organs can be measured using the flexible probe 2. The flexible probe 2 can be placed in and around the shield to measure the absorbed dose. Once again the sensor 4 can be read in real time or as a passive beam check.

(iv) Radiosurgery.

Radiosurgery is a technique that employs accurate stereotactic localization of intracranial targets and allows accurate deposition of a single high dose of radiation to the target volume, while minimizing dose to the surrounding brain structure. Very small volumes are treated with radiosurgery ranging from less than 1 cc to a few cc. This ability of precise tumour and treatment localization and the use of small beams creates steep dose gradients. It is possible to measure absorbed dose using a flexible probe 2 and circuit. It is very important that tissue just a few millimeters from the targeted volume receives insignificant dose. The inventor is not aware of other direct-reading dosimeters on the market at this time that are capable of the spatial resolution that is needed for radiosurgery. To date patient's planned treatments are calculated through computer simulations.

(v) Conductive interstitial hyperthermia.

The goal for hyperthermia is to raise tumour temperature above a cytotoxic threshold for an extended period of time without harmful elevation of surrounding normal tissue temperatures. The flexible probe 2 can be used to measure absorbed dose when the patient is undergoing hyperthermia treatments. The response of the flexible probe 2 is independent of temperature, and is therefore ideal for this procedure.

The flexible probe 2 may be used in the same manner as standard packaged MOSFET dosimeters with the following perceived advantages:

(i) The spatial resolution of the flexible probe dosimeter has been substantially improved. The sensor 2 area (MOS dosimeter plus surrounding package) is 2.2 mm×2 mm. The flexible circuit is 1 mm thick while its present length is 24.4 cm. The size of the flexible dosimeter makes dosimetry for radiosurgery possible.

(ii) The flexible probe dosimeter is capable of being inserted into a catheter. The very nature of the flexible circuit allows it to be bent into many configurations. It is therefore possible to place the sensitive area of the flexible dosimeter within areas of the body that were heretofore difficult to reach.

(iii) The sensitive area of the flexible dosimeter can also be placed within a water tank without fear of destroying the MOS dosimeter. Since the flexible dosimeter has been designed to be placed within the body for in vivo measurements its advantage over other types of dosimetry is its humidity independence.

(iv) The flexible probe can be configured as a passive dosimeter or as a direct reading dosimeter. The advantage of the passive dosimeter is that there are a reduced number of cables connecting it to a readout circuit, thus minimizing the material that is placed within or near the radiation beam. In direct reading mode the radiation beam can be monitored in real time. This has the advantage of decreasing the set up time for patient planning. Absorbed dose can be monitored at a specific point within a phantom, and the beam can be modified and subsequent measurements can be made without disassembling the phantom.

(v) Beam quality checks can be made with the flexible circuit placed in an array. The configuration of the array is left to the user.

Figure 8:
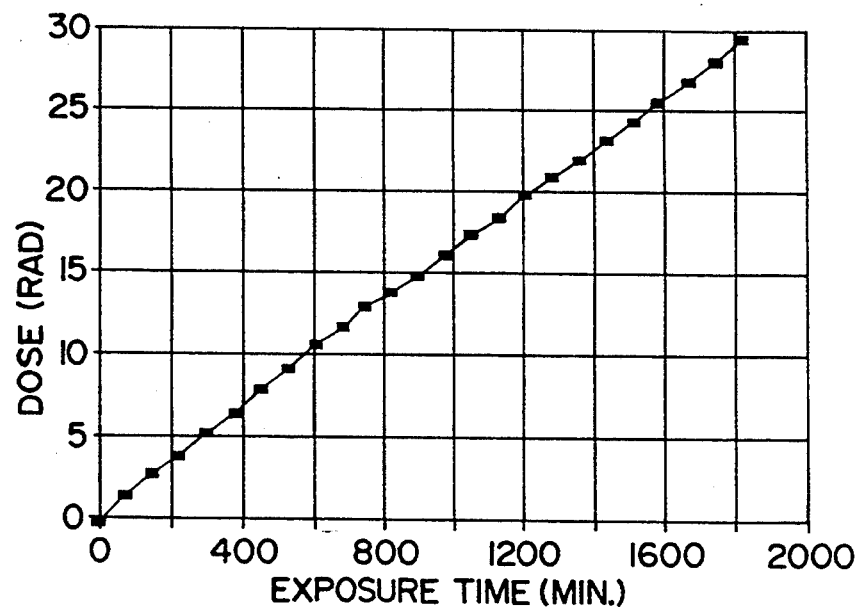
FIG. 8 is a graph showing the correlation between a dose measured by a direct dosimeter as a function of exposure time for a dosimeter according to the present invention.

It has been found that the radiation performance of the flexible probes 2 with respect to sensitivity, linearity, temperature dependence, and dose rate are similar to that of other packaged MOS devices and more particularly as described in U.S. Pat. No. 5,117,113. Referring to FIG. 8, results of a direct reading flexible probe are shown where the radiation data was recorded in a data recorder 30 as shown in FIG. 7.

While the invention has been described in connection with a specific embodiment thereof and in a specific use, various modifications thereof will occur to those skilled in the art without departing from the spirit and scope of the invention as set forth in the appended claims.

The terms and expressions which have been employed in the specification are used as terms of description and not of limitations, and there is no intention in the use of such terms and expressions to exclude any equivalents of the features shown and described or portions thereof, but it is recognized that various modifications are possible within the scope of the claims to the invention.

The embodiments of the invention in which an exclusive property of privilege is claimed are defined as follows:

1. A flexible radiation probe comprising:
   a semiconductor substrate with a pair of insulated gate field effect transistors integrated into said semiconductor substrate, each having a gate, source and drain; and
   an elongated flexible member having:
   a first end for supporting said semiconductor substrate,
   a second end remote to said first end, said second end being provided with connecting means for electrical connection to external circuitry, and
   conductor means provided in said flexible member for connecting said gate, source and drains of each of said transistors to said connecting means.

2. A probe as defined in claim 1, said first end including a rigid member for mounting said semiconductor substrate thereon.

3. A probe as defined in claim 1, wherein said first end is provided with a rigid member having said semiconductor substrate fixed thereof, a plurality of bonding pads arranged around said semiconductor substrate, for connecting said source, drain and gate of each of said transistors to a respective one of said bonding pads.

4. A probe as defined in claim 3, said semiconductor substrate and said bonding pads being covered with a suitable epoxy.

5. A probe as defined in claim 1, said semiconductor substrate being surrounded along its edges by a wall of insulating material.

6. A probe as defined in claim 5, including a metal cover arranged over the top surface of said semiconductor and being supported by said wall.

7. A probe as defined in claim 6, said metal cover being metallised mylar.

8. A probe as defined in claim 6, said metal cover being a foil of aluminum.

9. A probe as defined in claim 5, said metal cover having a thickness of 7 mg/cm$^2$.

10. A probe as defined in claim 1, said external circuitry including means for differentially biasing said transistors and means for reading a differential threshold voltage between said transistors.

11. A probe as defined in claim 1, said conductor means including a plurality of electrically conductive tracks, each extending between said first and second ends.

12. A probe as defined in claim 11, said tracks being copper.

13. A probe as defined in claim 1, said tracks each being 0.01 inches wide and having a thickness in the range of 0.002 to 0.01 cm.

14. A probe as defined in claim 3, wherein each of said tracks is enlarged at said first and said second end to form a first and a second pad, each of said first pads being connected to a bonding pad.

15. A probe as defined in claim 11, said flexible member being a multilayer circuit board.

16. A probe as defined in claim 15, in which said multilayer circuit board is composed of alternately superposed layers of polyimide film and layers of said connection tracks.

17. A probe as defined in claim 16, said polyimide being Kapton.

18. A probe as defined in claim 1, in which the width of said flexible member is smaller than a diameter of a catheter so that said flexible radiation probe may be inserted into said catheter.

19. A radiation dosimeter comprising:
   a flexible member having a plurality of electrical connection tracks extending between first and second ends thereof;
   a semiconductor radiation sensor supported on said first end of said flexible member, said sensor having a pair of insulated gate field effect transistors integrated into a semiconductor substrate each having a gate, source and drain, and said electrical connection tracks for connecting to a respective one of said source, drain and gate; and
   terminal means at said second end for receiving a differentially biasing signal so that one of said transistors is more sensitive to ionizing radiation than the other of said transistors during exposure of said transistors to radiation.

20. A dosimeter as defined in claim 19, including reader means connectable to said second end of said flexible member for reading out the differential threshold voltage between said transistors after irradiation, said differential threshold voltage being indicative of the radiation received by said transistors.

21. A dosimeter as defined in claim 19, said biasing means being a battery.

22. A dosimeter as defined in claim 19, said biasing means including a memory means for storing user information and dosimeter information.

23. A dosimeter as defined in claim 22, said memory means being an EEPROM.

24. A dosimeter as defined in claim 22, said reader including a visual display for displaying said radiation dose.

25. A dosimeter as defined in claim 19, said flexible member further including a fastening tab at said first end for attaching said first end to a predetermined position on body.

26. A radiation dosimeter comprising:
   flexible means having a plurality of electrical connection tracks extending between first and second ends thereof;

a radiation sensor supported on said first end of said flexible means, said sensor having a pair of insulated gate field effect transistors integrated into a semiconductor substrate each having a gate, source and drain, said electrical connection tracks connecting said source, drain and gate to said second end; and terminal means at said second end for periodically receiving a biasing signal and for transmitting a reading signal indicative of the differential threshold voltage between said transistors.

27. A method for monitoring of radiation applied to a patient's body comprising the steps of:
(a) inserting into the patient's body a flexible radiation probe having a flexible member including a plurality of electrical connection tracks extending between first and second ends thereof and a radiation sensor supported at a first end of said flexible member, said sensor having a pair of insulated gate field effect transistors integrated into a semiconductor substrate each having a gate, source and drain, said electrical connection tracks connecting said source, drain and gate to said second end;
(b) irradiating the body and differentially biasing said transistors by a bias source connected at said second end of said flexible member through said connection tracks;
(c) disconnecting said bias source from said second end of said flexible member after a predetermined time period; and
(d) reading out the differential threshold voltage between said transistors with a read out means connected at said second end of said flexible member through said connection tracks.

28. A method as defined in claim 10 wherein said probe is inserted into a catheter.

29. A method for monitoring of radiation applied to a body comprising the steps of:
(a) inserting into the body a flexible radiation probe having a flexible member including a plurality of electrical connection tracks extending between first and second ends thereof and a radiation sensor supported at a first end of said flexible member, said sensor having a pair of insulated gate field effect transistors integrated into a semiconductor substrate each having a gate, source and drain, said electrical connection tracks connecting said source, drain and gate to said second end;
(b) periodically biasing said transistors differentially and reading out the differential threshold voltage between said transistor through said flexible member.

30. A method of claim 29 further comprising inserting said probe into a catheter.

31. A method of claim 27 wherein step (a) comprises providing a plurality of radiation sensors each mounted on flexible means and step (b) comprises inserting said sensors at a predetermined distance apart from each other so as to measure the profile of a radiation beam.

32. A method for monitoring of radiation applied to an extremity of a body comprising the steps of:
(a) providing a flexible radiation probe having a flexible member including a plurality of electrical connection tracks extending between first and second ends thereof and a radiation sensor supported at a first end of said flexible member, said sensor having a pair of insulated gate field effect transistors integrated into the same substrate each having a gate, source and drain, said electrical connection tracks connecting said source, drain and gate to said second end;
(b) attaching said first end with said sensor, to said extremity by way of a fixing tab;
(c) connecting said second end to a means for differentially biasing said transistors; and
(d) reading out the differential threshold voltage between said transistors by a reader means, said differential threshold voltage being indicative of a radiation dose received at said extremity.

33. A probe as defined in claim 5, including a metal cover arranged over the top surface of said semiconductor substrate and being supported by said wall.

34. A probe as defined in claim 33, said metal cover being metallised mylar.

35. A probe as defined in claim 33, said metal cover being a foil of aluminum.

36. A probe as defined in claim 33, said metal cover having a thickness of 7 mg/cm$^2$.

37. A probe as defined in claim 32, said semiconductor being covered with a suitable epoxy.

* * * * *